(12) United States Patent
Ra et al.

(10) Patent No.: US 7,550,577 B2
(45) Date of Patent: Jun. 23, 2009

(54) REGULATION OF EXPRESSION OF HIGH-AFFINITY IMMUNOGLOBULIN E (IGE) RECEPTOR β-CHAIN

(75) Inventors: Chisei Ra, Tokyo (JP); Kyoko Takahashi, Tokyo (JP)

(73) Assignee: Nihon University, Tokyo (JP)

(*) Notice: Subject to any disclaimer, the term of this patent is extended or adjusted under 35 U.S.C. 154(b) by 311 days.

(21) Appl. No.: 10/559,265

(22) PCT Filed: Jun. 4, 2003

(86) PCT No.: PCT/JP03/07086

§ 371 (c)(1),
(2), (4) Date: Dec. 2, 2005

(87) PCT Pub. No.: WO2004/108929

PCT Pub. Date: Dec. 16, 2004

(65) Prior Publication Data

US 2007/0081990 A1    Apr. 12, 2007

(51) Int. Cl.
*C07H 21/04* (2006.01)
*C12N 15/63* (2006.01)

(52) U.S. Cl. .................. 536/24.1; 435/320.1; 536/23.1

(58) Field of Classification Search .................. None
See application file for complete search history.

(56) References Cited

U.S. PATENT DOCUMENTS

| | | | | |
|---|---|---|---|---|
| 5,770,396 A | * | 6/1998 | Kinet | 435/69.1 |
| 5,962,406 A | * | 10/1999 | Armitage et al. | 514/8 |
| 6,090,620 A | * | 7/2000 | Fu et al. | 435/325 |
| 6,171,803 B1 | * | 1/2001 | Kinet | 435/7.1 |
| 7,034,007 B1 | * | 4/2006 | Nyce et al. | 514/44 |

OTHER PUBLICATIONS

S. Lin et al., Cell, vol. 85, pp. 985-995, (1996).
D. Domobrowicz et al., Immunity vol. 8, pp. 517-529, (1998).
E. Donnadieu et al., Immunity, vol. 2, pp. 515-523, (2000).
H. Kuster et al., J. Biol. Chem. 267, No. 18, pp. 12782-12787, (1992).
Y. Akizawa et al., Int. Immunol. vol. 15, pp. 549-556, (2003).
R. Hromas, etal., Cuur. Top. Microbiolo. Immunol., vol. 211, pp. 159-164, (1996).
K. Takahashi et al., The 25th Annual Meeting of the Molecular Biology Society of Japan, vol. 25, Dec. 11, 2002, p. 611, 1P-1129.
K. Takahashi et al., Proceedings of the Japanese Society for Immunology, vol. 32, Dec. 4, 2002, p. 261, 3-D-W40-13-P.
Bavisotto L. et al., Antisense Oligonucleotides from the Stage-Specific Myeloik Zinc Finger Gene MZF-1 Inhibit Granulopoiesis In Vitro., J.Exp.Med., 1991, vol. 174, pp. 1097-1101.

* cited by examiner

*Primary Examiner*—Q. Janice Li
(74) *Attorney, Agent, or Firm*—Morgan Lewis & Bockius LLP

(57) ABSTRACT

The present invention provides a polynucleotide comprising all or a part of the nucleotide sequence identified as SEQ ID NO:1 that regulates transcription of the human high-affinity IgE receptor (FcεFI) β-chain gene, and a method for regulating transcription of the FcεFI β-chain gene which comprises the step of promoting binding between a transcription regulatory complex containing MZF-1 and the transcription regulatory region of the FcεFI β-chain gene that contains the nucleotide sequence identified as SEQ ID NO: 1. In addition, the present invention provides a screening method and a kit therefor that utilizes the method for regulating transcription of the FcεFI β-chain gene having the step of promoting binding between a transcription regulatory complex containing MZF-1 and the transcription regulatory region of the FcεFI β-chain gene that contains the nucleotide sequence identified as SEQ ID NO:1, thereby enabling development of a novel agent for the prevention and treatment of allergic diseases.

4 Claims, 5 Drawing Sheets

1: pCR3.1-self (empty vector)
2: pCR3.1-hMZF1antisense

SEQUENCE LISTING

```
<160> NUMBER OF SEQ ID NOS: 9

<210> SEQ ID NO 1
<211> LENGTH: 24
<212> TYPE: DNA
<213> ORGANISM: Homo sapiens

<400> SEQUENCE: 1
gtgagttgcc cgyttctgtc tttg                                          24

<210> SEQ ID NO 2
<211> LENGTH: 24
<212> TYPE: DNA
<213> ORGANISM: Artificial sequence
<220> FEATURE:
<223> OTHER INFORMATION: Synthetic oligo DNA

<400> SEQUENCE: 2
gtgagttgcc cgcttctgtc tttg                                          24

<210> SEQ ID NO 3
<211> LENGTH: 24
<212> TYPE: DNA
<213> ORGANISM: Artificial sequence
<220> FEATURE:
<223> OTHER INFORMATION: Synthetic oligo DNA

<400> SEQUENCE: 3
caaagacaga agcgggcaac tcac                                          24

<210> SEQ ID NO 4
<211> LENGTH: 25
<212> TYPE: DNA
<213> ORGANISM: Artificial sequence
<220> FEATURE:
<223> OTHER INFORMATION: Primer

<400> SEQUENCE: 4
```

```
atgaatggtc cccttgtgta tgcag                                         25

<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5
ctactcggcg ctgtggacgc gctggt                                        26

<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6
atggacacag aaagtaatag gagag                                         25

<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
cttataaatc aatgggagga gacatt                                        26

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
catcgagcac ggcatcgtca ccaac                                         25

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gtgttggcgt acaggtcttt gcgga                                         25
```

REGULATION OF EXPRESSION OF HIGH-AFFINITY IMMUNOGLOBULIN E (IGE) RECEPTOR β-CHAIN

TECHNICAL FIELD

The present invention relates to regulation of expression of the high-affinity immunoglobulin E (IgE) receptor β-chain, and more particularly to the repression of transcription of the high-affinity IgE receptor β-chain gene and the use thereof.

BACKGROUND ART

The number of people with allergic conditions such as pollinosis, atopic dermatitis, and atopic asthma has increased in recent years, and this has become a problem in society. These allergic diseases are classified as type I allergy that is mediated by IgE.

The high-affinity IgE receptor (hereinafter, FcεFI) expressed on the membrane of mast cells and basophils is known to be a key glycoprotein in type I allergic reaction. When antigen-specific IgE bound to FcεFI is crosslinked by its corresponding multivalent antigen (for example, Japan cedar pollen in patients with Japan cedar pollinosis, dust mite antigen in patients with dust mite allergy, etc.), the FcεFI aggregates, signal transduction cascades are initiated, and initial activation of mast cells occurs. The result is an explosive release of various chemical substances that cause allergic inflammation, more specifically, the initial release of histamine that has already been stored in intracellular granules is followed by the new synthesis and release of leukotrienes, prostaglandins, and other intracellular metabolites, manifesting thereby in type I allergic reaction.

Furthermore, synthesis and secretion of cytokines from mast cells are induced by aggregation of FcεFI on the mast cell, and these cytokines induce expression of various adhesion molecules in nearby vascular endothelial cells. Mediated by these adhesion molecules, eosinophils and lymphocytes in the blood bind to vascular endothelial cells at the site of inflammation and accumulate. As a result, a late asthmatic response occurs. Furthermore, the FcεFI expressed in Langerhans cells in the skin is thought to be involved in the pathogenesis of atopic dermatitis through antigen presentation, cytokine production, etc.

Based on the above knowledge, a promising strategy for the development of agents for prevention and treatment of allergic diseases is to target FcεFI, which specifically mediates type I allergy, and to interrupt signal transduction from this receptor at its source.

In humans the FcεFI protein is expressed on the cell surface and functions either as a tetramer consisting of an α-chain, β-chain, and two γ-chains, or a trimer consisting of an α-chain and two γ-chains. The α-chain binds directly to IgE through its extracellular domain, while the β-chain and γ-chains are involved in intracellular signal transduction. Among these subunits, the β-chain not only plays an important role in amplifying the signal mediated by the γ-chains (see, for example, non-patent documents 1 and 2), but recently it has been reported that the β-chain enhances the expression of cell surface FcεFI by promoting the maturation of the α-chain (see, for example, non-patent document 3). This means that the inhibition of β-chain expression will reduce the expression of these receptors on the cell surface and attenuate the intensity of the intracellular signal that is transduced by each individual receptor. It is expected that inhibition of the expression of this β-chain can control allergic reaction very effectively.

Specific repression of transcription of the β-chain gene is a useful method for inhibiting expression of the FcεFI β-chain.

The genomic structure and nucleotide sequence of the human FcεFI β-chain gene have already been determined (see, for example, non-patent document 4). However, analysis has been performed only on the region upstream of the start codon that contains the promoter region, and it has been reported that a region containing an Oct-1 binding motif is essential for promoter activity (see non-patent document 5).

However, a transcription regulatory region has not been specifically identified in another region of the gene, and because there are many instances in which a transcription regulatory region is present in an intron or an untranslated region on the 3' side of a gene, it is possible that a region that regulates transcription of the FcεFI β-chain gene is present in a region of the gene that has not yet been analyzed.

[Non-patent document 1]
S. Lin et al., Cell 85, 985-995 (1996)
[Non-patent document 2]
D. Domobrowicz et al., Immunity 8, 517-529 (1998)
[Non-patent document 3]
E. Donnadieu et al., Immunity 12, 515-523 (2000)
[Non-patent document 4]
H. Kuster et al., J. Biol. Chem. 267, 12782-12787 (1992)
[Non-patent document 5]
Y. Akizawa et al., Int. Immunol. 15, 549-556 (2003)

DISCLOSURE OF THE INVENTION

In view of the above circumstances, an object of the present invention is to specify a region involved in the regulation of transcription of the human FcεFI β-chain gene from among the regions that have yet to be analyzed, and a further object of the present invention is to specify a transcription factor that binds thereto. The present invention has been completed through knowledge of a region involved in the regulation of transcription of the human FcεFI β-chain gene and a transcription factor that binds thereto.

More specifically, the present invention provides:

(1) a polynucleotide comprising a part or all of the nucleotide sequence identified as SEQ ID NO: 1 that regulates the transcription of the human high-affinity immunoglobulin E receptor β-chain gene;

(2) the polynucleotide according to item (1), wherein the polynucleotide is DNA;

(3) a method for regulating the transcription of the human high-affinity immunoglobulin E receptor β-chain gene, comprising the step of promoting binding between MZF-1 and the transcription regulatory region of the human high-affinity immunoglobulin E receptor β-chain gene that contains the nucleotide sequence identified as SEQ ID NO: 1;

(4) a method for regulating the transcription of the human high-affinity immunoglobulin E receptor β-chain gene, comprising the step of promoting binding between a transcription regulatory complex containing MZF-1 and the transcription regulatory region of the human high-affinity immunoglobulin E receptor β-chain gene that contains the nucleotide sequence identified as SEQ ID NO: 1;

(5) a method of screening for compounds or salts thereof that promote binding between MZF-1 and the transcription regulatory region of the human high-affinity immunoglobulin E receptor β-chain gene that contains the nucleotide sequence identified as SEQ ID NO: 1;

(6) a method of screening for compounds or salts thereof that promote binding between a transcription regulatory complex containing MZF-1 and the transcription regulatory region of the human high-affinity immunoglobulin E receptor β-chain gene that contains the nucleotide sequence identified as SEQ ID NO: 1;

(7) a screening kit for compounds or salts thereof that regulate the transcription of the human high-affinity immunoglobulin E receptor β-chain gene, said kit utilizing a polynucleotide comprising a part or all of the nucleotide sequence identified as SEQ ID NO: 1;

(8) a compound or salt thereof that regulates the transcription of the human high-affinity immunoglobulin E receptor β-chain gene and is obtained by the screening method according to items (5) or (6), or the screening kit according to item (7);

(9) a medicine containing the compound or salt thereof according to item (8);

(10) the medicine according to item 9, wherein the medicine is an agent for the prevention or treatment of an allergic disease;

(11) a method for the prevention and treatment of an allergic disease comprising the step of administering to a mammal an effective dose of the compound or salt thereof according to item (8); and

(12) a use of the compound or salt thereof according to item (8) to manufacture an agent for the prevention and treatment of an allergic disease.

BEST MODE FOR CARRYING OUT THE INVENTION

Figure 1:
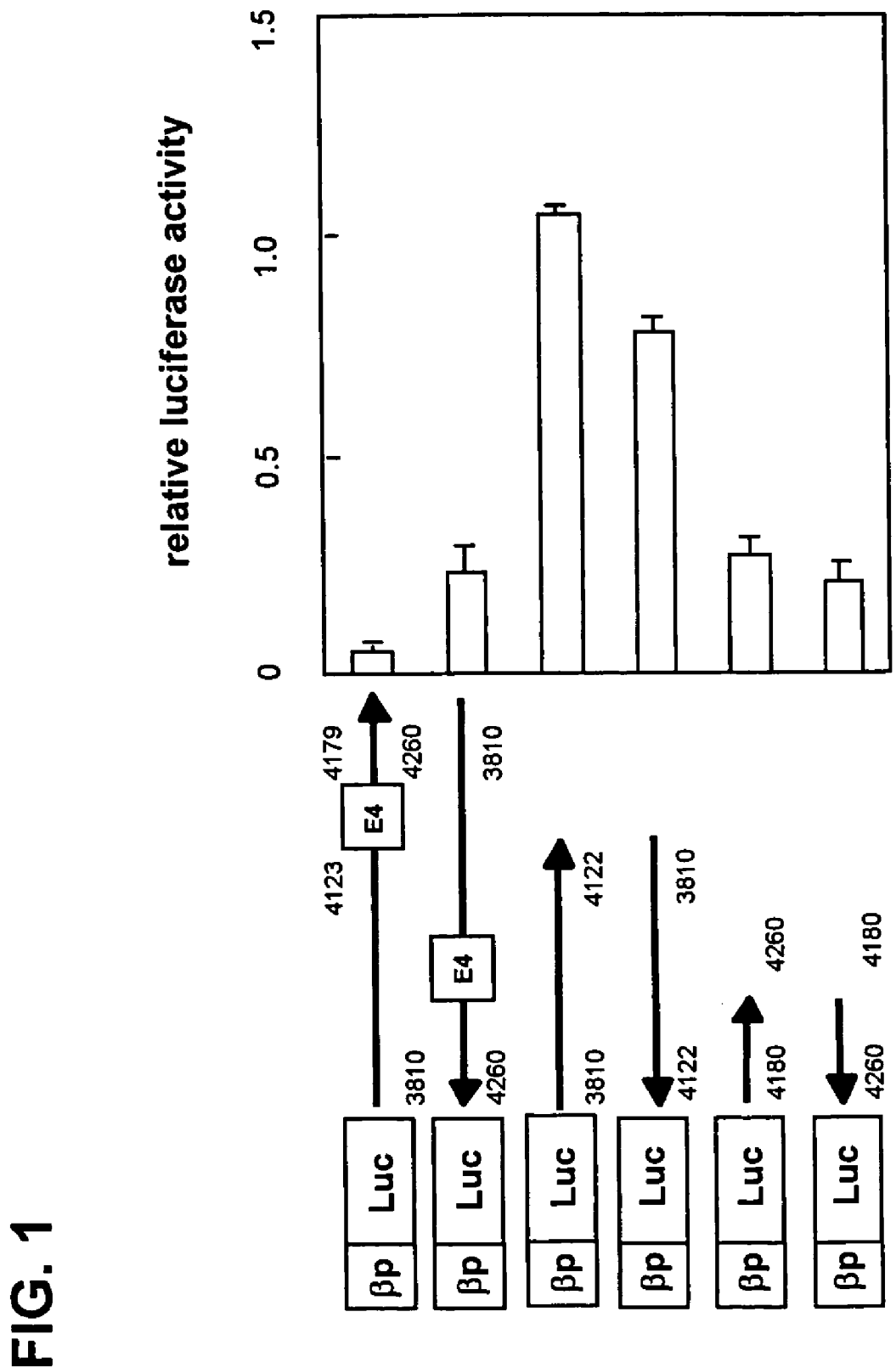
FIG. 1 shows the results of measurement of transcription regulatory activity of the nt4180-nt4260 region of the human FcεFI β-chain gene by reporter assay in the present invention.

Next the modes for carrying out the present invention will be described. The following embodiment is an example to describe the present invention, and the present invention is by no means restricted to this embodiment alone. The present invention can be carried out in a variety of modes, provided those modes do not deviate from the spirit of the invention.

DNA containing a region that regulates the transcription of the human high-affinity IgE receptor (FcεFI) β-chain gene of the present invention was obtained by the method described below.

First, it was discovered by reporter gene assay that a region corresponding to part of intron 4 that lies between exon 4 and exon 5 on the human FcεFI β-chain gene represses transcription of the FcεFI β-chain gene. In addition, it was revealed by site-directed mutagenesis that the sequence in intron 4 identified as SEQ ID NO: 1, which is homologous with the MZF-1 binding motif, is actually involved in transcriptional repression. Next, the transcription regulatory factor that binds to the sequence identified as SEQ ID NO: 1, which is the transcription regulatory region, was identified. The fact that MZF-1 actually binds to this sequence was determined by gel shift assay using nuclear extracts prepared from cells expressing FcεFI β-chain. In addition, it was confirmed that the transcription regulatory factor MZF-1 actually represses transcription of the FcεFI β-chain gene from the fact that the FcεFI β-chain gene promoter activity increased and the amount of FcεFI β-chain mRNA increased when an MZF-1 antisense expression vector was introduced into cells expressing the FcεFI β-chain.

Thus, because a DNA region involved in the regulation of transcription of the FcεFI β-chain gene and a transcription regulatory factor binding to the region have been identified, a method of screening for a compound or a salt thereof that inhibits FcεFI β-chain expression and a screening kit therefor can be prepared, and the above discovery may consequently serve as a resource for the development of agents for prevention and treatment of allergic diseases. For example, by pursuing a policy of searching for substances that promote binding between the identified transcription regulatory factor MZF-1 and the specified region of the gene, it may be possible to develop a compound or salt thereof that inhibits β-chain expression.

It has been reported that the transcription regulatory factor MZF-1 functions in both transcription activation and transcription repression depending on the type of cell and promoter structure of the gene, which implies the existence of transcription activatory and repressive cofactors (R. Hromas, et al., Cuur. Top. Microbiolo. Immunol., 211, 159-164 (1996)). Therefore, it is possible that MZF-1 is involved in the repression of transcription through binding with other cofactors, and by pursuing a policy of searching for substances that promote this interaction, it will be possible to develop the compound or the salt thereof that inhibits β-chain expression. For example, a method of screening for natural and synthetic compounds that repress FcεFI β-chain transcription can be provided by introducing a reporter plasmid containing the nt4180-nt4260 region of the β-chain gene described below in Example 1 of the present invention into suitable cells that express the FcεFI β-chain and using the decrease in luciferase activity as an indicator. In addition, it is possible to search for compounds or salts thereof that promote formation of a transcription repressive complex containing MZF-1 by using a partial peptide of MZF-1 and the region containing the sequence identified as SEQ ID NO: 1 by using a partial peptide of MZF-1 corresponding to its binding region with cofactor.

The term "salt of a compound" used herein refers to a salt of a physiologically acceptable acid (for example, an inorganic acid, organic acid, etc.) and a physiologically acceptable base (for example, an alkali metal, etc.). A physiologically acceptable acid addition salt is especially preferred. Specific examples of this salt include salts of inorganic acids such as hydrochloric acid, phosphoric acid, hydrobromic acid, and sulfuric acid, or of organic acids such as acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.

Compounds or salts thereof regulating transcription of the FcεFI β-chain gene that are obtained using the screening method and screening kit of the present invention will be useful as agents for prevention and treatment of allergic diseases. Medicine containing the aforementioned compounds or salts thereof will have an especially high utility value.

The compound or salt thereof obtained in accordance with the present invention can be used as needed either orally as a sugar-coated tablet, capsule, microcapsule, etc., or parenterally in the form of an injection such as a sterile solution or suspension in water or another pharmaceutically acceptable liquid. For example, the compound or salt thereof obtained in accordance with the present invention can be made into a manufactured product by admixture with a physiologically acceptable carrier, flavoring, excipient, vehicle, preservative, stabilizer, binder, etc., in the form of a unit dose generally expected in recognized pharmaceutical manufacturing methods. The content of active ingredient in these pharmaceutical preparations will be adjusted so that a suitable dose in the indicated range can be obtained. For example, binders such as gelatin, cornstarch, tragacanth, gum arabic, etc.; fillers such as crystalline cellulose; swelling agents such as cornstarch, gelatin, alginic acid, etc.; lubricants such as magnesium stearate; sweeteners such as sucrose, lactose or saccharin; and flavorings such as peppermint, "Akamono" (*Gaultheria adenothrix*) oil, or cherry can be used as additives that can be mixed into tablets, capsules, etc. When the formulation unit is a capsule, a liquid carrier such as an oil can be included in addition to the aforementioned types of ingredients. A sterile composition for injection can be formulated in accordance with conventional pharmaceutical manufacturing methods, for example, dissolving or suspending the active ingredient, and a natural vegetable oil such as sesame oil, etc., in a vehicle such as an injection solvent. Water-based injection solvents include, for example, physiological saline and isotonic liquids containing glucose and other adjuvants (for example, D-sorbitol, D-mannitol, sodium chloride, etc.) A suitable solubilizer, for example, an alcohol (ethanol, etc.) or polyalcohol (for example, propylene glycol, polyethylene glycol, etc.), and nonionic surfactant (for example, polysorbate 80®, HCO-50, etc.) can also be used. Solubilizers include, for example, sesame oil, soybean oil, etc., and they may be used together with benzyl benzoate, benzyl alcohol, etc., as solubilizers. In addition, buffers (for example, phosphate buffer, sodium acetate buffer, etc.); soothing agents (for example, benzalkonium chloride, procaine hydrochloride, etc.); stabilizers (for example, human serum albumin, polyethylene glycol, etc.); preservatives (for example, benzyl alcohol, phenol, etc.); and antioxidants may also be included. The formulated injection is conventionally packaged in a suitable ampule.

Because a pharmaceutical preparation obtained in the above manner is safe and has low toxicity, it can be administered to mammals and warm-blooded animals (for example, humans, rats, mice, guinea pigs, and rabbits). The dose of the compound or salt thereof obtained in accordance with the present invention will vary depending on the disease to be treated, recipient of the dose, route of administration, etc., but when the compound or salt thereof obtained in accordance with the present invention is administered orally for the purpose of treating pollenosis, for example, generally speaking an adult (60 kg) will be administered a dose of 0.1 mg to 1.0 g, preferably a dose of approximately 1.0 mg to 50 mg, of the compound or salt thereof each day.

The present invention is described below in detail through examples, but the present invention is in no way limited to these examples.

EXAMPLE 1

Measurement of Transcription Regulatory Activity of the nt4180-nt4260 Region of the Human FcεFI β-chain Gene FcεFI β-chain gene fragments were obtained from a human genomic library (Stratagene) by plaque hybridization. Gene fragment nt4180-nt4260 containing a part of intron 4 that was obtained using restriction enzyme digestion and PCR technique was inserted downstream of the human FcεFI β-chain promoter in an expression plasmid encoding luciferase as the reporter gene.

To suspensions of KU812 human cell line ($1 \times 10^7$ cells) expressing the FcεFI β-chain in 500 µl of medium (RPMl (Invitrogen) containing 20% FCS), either 5 µg of the aforementioned reporter plasmid or 0.1 µg of the pRL-CMV plasmid (Toyo Ink) that encodes the sea pansy luciferase gene under the control of the CMV promoter as a control were added; then electroporation (300 V, 950 µF) was performed using a Gene Pulser II (Bio-Rad). Half the volume of each suspension was transferred to a 12-well plate to which 2 mL of medium per well was added, and the cells were cultured at 37° C. under a 5% $CO_2$ atmosphere for 24 hours. The cells were collected, and after the addition of a cytolysis solution, the activities of firefly luciferase and sea pansy luciferase were measured using a Luminometer (Berthold). The cytolysis solution and substrate used were included in a Dual luciferase assay kit (Promega). The value of firefly luciferase activity/sea pansy luciferase activity was calculated for each sample.

FIG. 1 shows the relative activity when the firefly luciferase activity/sea pansy luciferase activity in the presence of the β-chain promoter only was assigned a value of 1.0.

In the results strong transcription repressive activity was seen with the nt4180-nt4260 gene fragment regardless of the direction of insertion.

EXAMPLE 2

Detailed Mapping of the Transcription Regulatory Element by Introduction of Site-specific Mutations Next, the transcription repressive sequence in the nt4180-nt4260 β-chain gene region was identified. Nucleotide substitutions of 3-5 bases were introduced in this region using a Quick Change Site-Directed Mutagenesis Kit (Stratagene), and luciferase assays were performed in the same manner as in Example 1 using reporter plasmids into which each of the site-specific mutations had been introduced.

Figure 2:
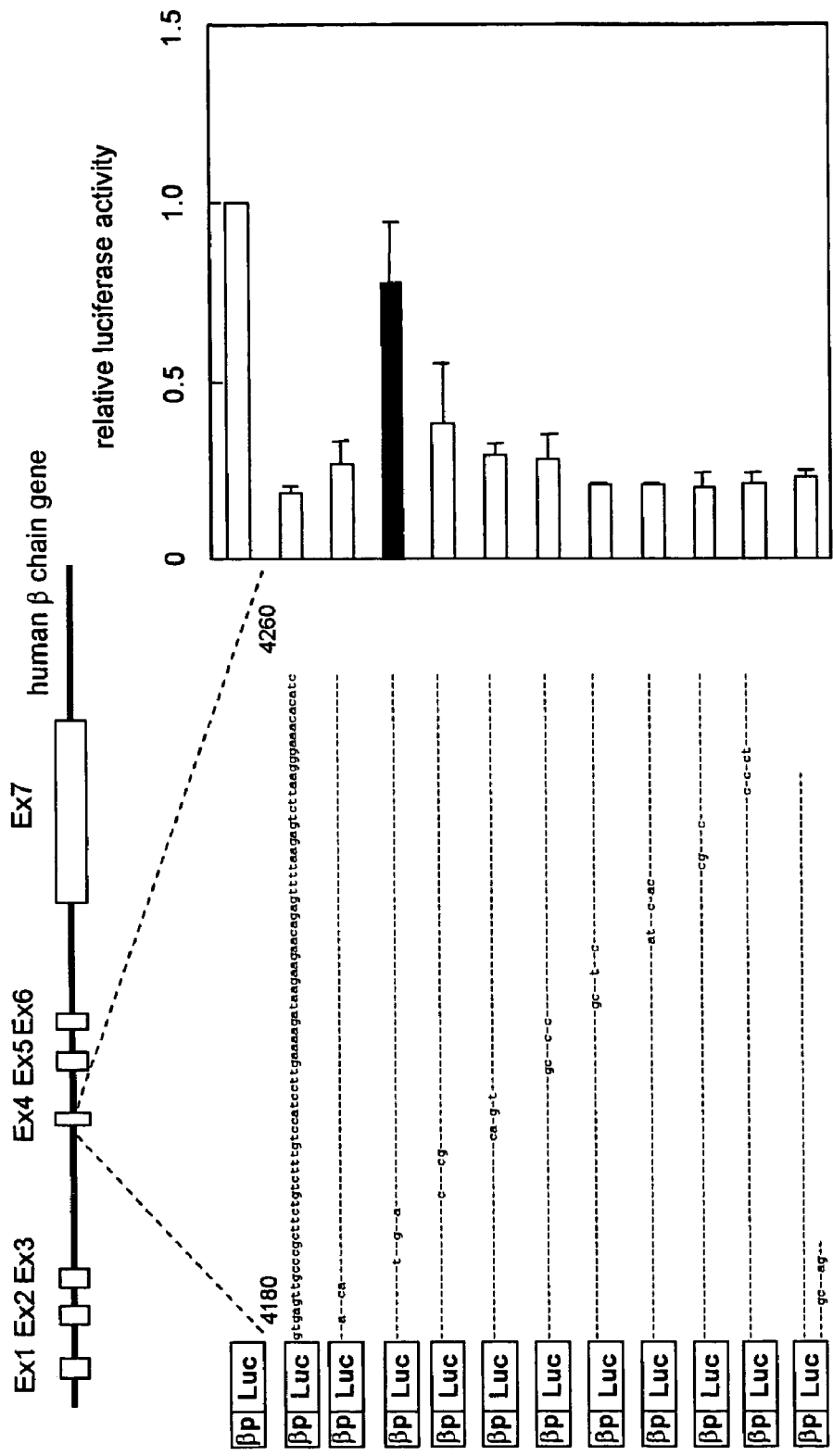
FIG. 2 shows the detailed mapping of the transcription regulatory element in the nt4180-nt4260 region by the introduction of site-specific mutations in the present invention.

As shown in FIG. 2, when a mutation was introduced in the vicinity of nt4190, the transcription repressive activity was blocked, and therefore it became clear that the sequence in the vicinity of nt4190 is essential for transcription repressive activity.

EXAMPLE 3

Identification of Binding Factor by Gel Shift Assay

A nuclear fraction was prepared from KU812 cells in the following manner. After the KU812 cells were collected, they were rinsed with ice-cold phosphate buffer (8 g NaCl, 0.2 g KCl, 0.2 g KH$_2$PO$_4$, and 2.9 g Na$_2$HPO$_4$.12H$_2$O in 1 L H$_2$O), and after the cells were suspended in a like manner in ice-cold buffer A (10 mM HEPES pH 7.9, 10 mM KCl, 0.1 mM EDTA, 1 mM DDT, 1 mM PMSF, 1 μg/mL leupeptin, 1 μg/mL aprotinin), the suspension was let stand on ice for 10 min. NP-40 was added to make a final concentration of 0.5%, and after the suspension was let stand for 15 min on ice, centrifugal separation was performed for 1 min at 6000 × g. The precipitated fraction was suspended in buffer E (20 mM HEPES pH 7.9, 400 mM KCl, 15 mM MgCl$_2$, 0.2 mM EDTA, 1 mM DTT, 1 mM PMSF, 1 μg/mL leupeptin, 1 μg/mL aprotinin), and after the suspension was let stand for 1 h on ice, centrifugal separation was performed for 10 min at 10000× g. The supernatant obtained by centrifugation was used as the nuclear fraction.

An isomolar mixture of FITC-labeled synthetic oligo DNA 5'-GTGAGTTGCCCGCTTCTGTCTTTG-3'(SEQ ID NO: 2) and 5'-CAAAGACAGAAGCGGGCAACTCAC-3'(SEQ ID NO: 3) (Invitrogen) was prepared, and after the mixture was let stand for 5 min at 95° C., it was allowed to cool slowly and then used as a probe. In addition, three species of unlabeled double-stranded synthetic oligo DNA, one with the same nucleotide sequence as the probe (self), one containing a three-base substitution in the vicinity of nt4190 (mutant), and one with a sequence that was unrelated to the probe (non-specific) were used as competitors.

Figure 3:
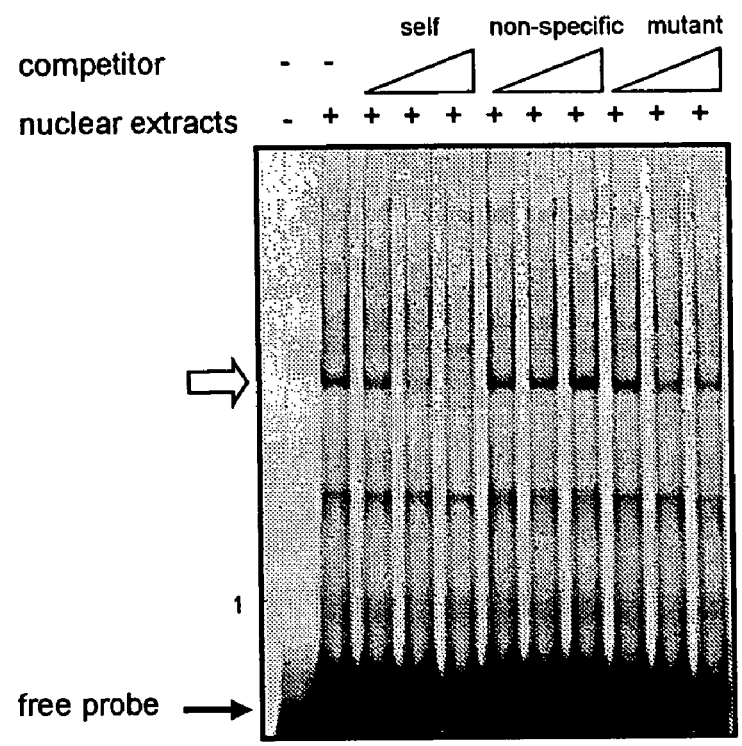
FIG. 3 shows identification of the binding factor by gel shift assay in the present invention. (A) shows a competitive test using unlabeled, double-stranded oligo DNA (the added unlabeled, double-stranded DNA is as follows: lanes 3-5; sequences identical to the probes, lanes 6-8; three-base substitutions in the probe sequences, lanes 9-11; nonspecific sequences), (B) shows a test using recombinant MZF-1 (lane 1; blank, lane 2; GST, lane 3; GST-MZF-1).
Figure 3:
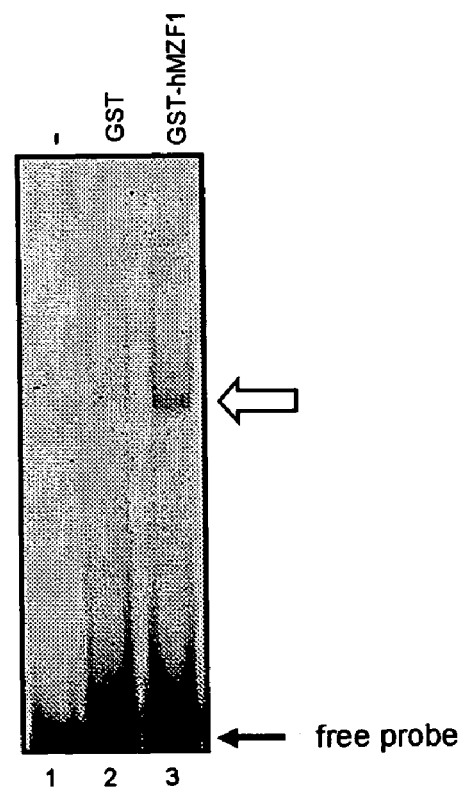

Mixtures containing 30 μg of the prepared nuclear extract, 5 pmol of probe, and 5-125 pmol of each competitor in 10 mM HEPES buffer (pH 7.9) containing 400 ng of poly (dl-dC), 1 mM MgCl$_2$, 30 mM KCl, 1 mM DTT, and 5% glycerol were prepared and let stand for 20 min at room temperature. The mixtures were separated on 4% polyacrylamide gel by electrophoresis using 0.5×TBE buffer (45 mM TRIS, 45 mM boric acid, 1 mM EDTA). After electrophoresis for 2-3 h at 120 V, the fluorescence of FITC was detected using a FluorImager 595 (Amersham Bioscience). FIG. 3(A) shows the results. Several shifted bands (lane 2) were observed at positions with less migration than the band of the probe alone, and among these the band indicated by the arrow disappeared in a competitor-concentration dependent manner when the self competitor was added (lanes 3-5), but was unaffected when the non-specific competitor was added (lanes 6-8). This difference shows that this band represents a condition in which the protein is specifically bound to the probe. In addition, it is clear that this protein recognizes and binds to a sequence in the vicinity of nt4190 because the extent of the competition becomes very weak when the mutant competitor is added (lanes 9-11).

The gene region in the vicinity of nt4190 contains a nucleotide sequence that is homologous with the transcription factor MZF-1 binding motif. Therefore, the transcription factor that binds to this sequence was identified. Normally, in a gel shift assay an antibody against MZF-1 is added to analyze whether super-shift or disappearance of the shifted bands occurs, but because there is no commercially available antibody against MZF-1, the analysis was performed using recombinant MZF-1 expressed by E. coli as a fusion protein with glutathione S-transferase (GST) (FIG. 3(B)). Shifted bands were seen when the GST-MZF-1 fusion protein was added to the probe, but shifted bands were not seen when only GST was expressed. Therefore, it was demonstrated that MZF-1 binds at the specified gene region in the vicinity of nt4190.

EXAMPLE 4

Increase of β-chain Promoter Activity in KU812 Cells by Introduction of an MZF-1 Antisense Next, in order to verify the transcription regulatory capability of the identified transcription factor in cells, MZF-1 antisense was introduced into KU812 cells, and the FcεFI β-chain promoter activity was measured under conditions in which the expression of the transcription factor was inhibited. First, the MZF-1 antisense was prepared as shown below. Total RNA was prepared from K562 cells using TRIZOL (Invitrogen). An RT reaction was performed using a random hexamer as a primer and 1 μg of total RNA as the template. Then, PCR was performed in a protocol of 30 cycles of 30 sec at 94° C., 30 sec at 65° C., and 2 min at 72° C. using the primers 5'-ATGAATGGTCCCCTTGTGTATGCAG-3'(SEQ ID NO: 4) and 5'-CTACTCGGCGCTGTG-GACGCGCTGGT-3'(SEQ ID NO: 5), which are specific to the human MZF-1 nucleotide sequence. The amplified fragments obtained thereby were inserted into a pCR3.1 vector (Invitrogen), clones into which a fragment running in the opposite direction to the CMV promoter had been inserted were selected based on the restriction enzyme cleavage pattern, the nucleotide sequence was verified, and the resulting plasmid was named pCR3.1-hMZF-1 antisense. In addition, a pCR3.1-self plasmid was prepared by cleaving pCR3.1 with EcoRI and then closing the loop with T4 ligase for use as a control.

Figure 4:
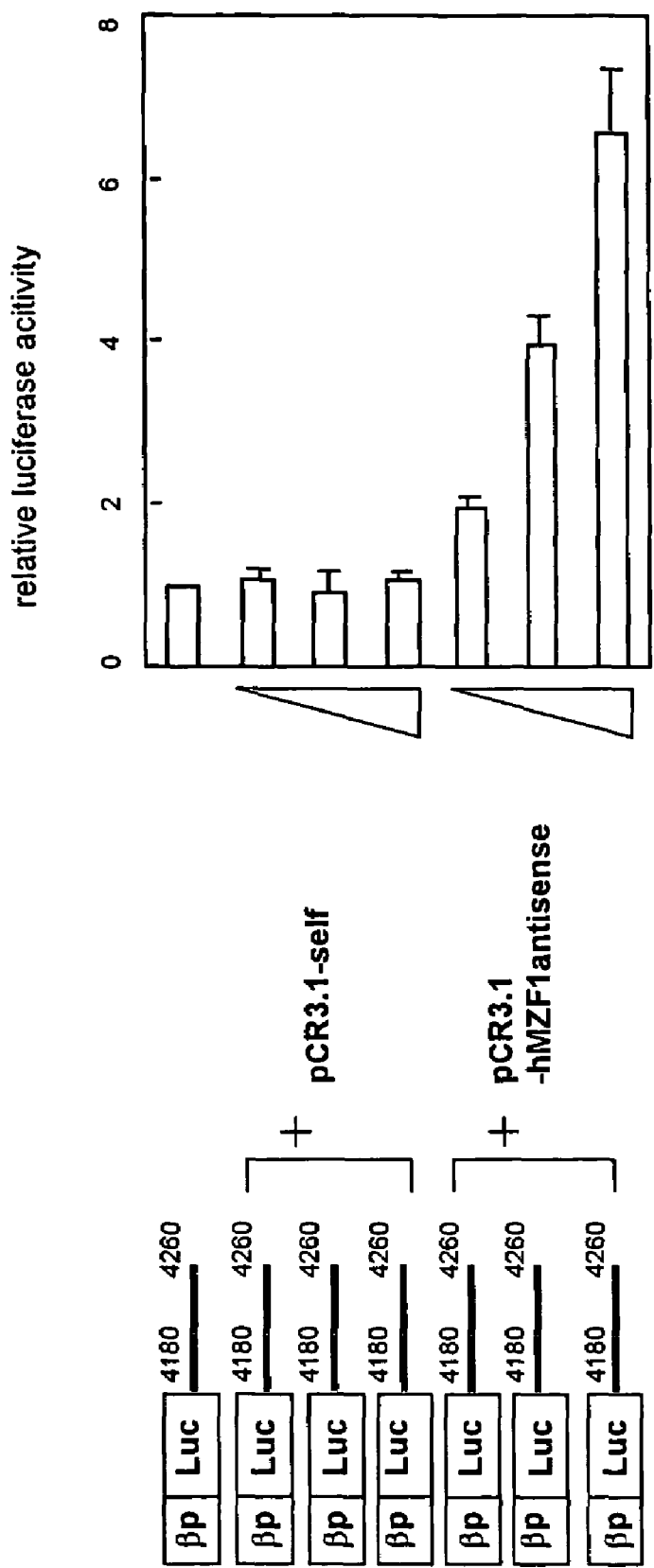
FIG. 4 shows an increase in human FcεFI β-chain gene promoter activity due to the introduction of an MZF-1 antisense in the present invention.

Amounts of 5-20 μg of the pCR3.1-hMZF-1 antisense or pCR3.1-self together with 5 μg of reporter plasmid containing the β-chain promoter and the nt4180-nt4260 region were inserted into KU812 cells by electroporation under the same conditions as those described in Example 1, and a luciferase assay was performed in the same manner. FIG. 4 shows the relative activity when the firefly luciferase activity/sea pansy luciferase activity in the presence of only the reporter plasmid was assigned a value of 1.0. The results show that luciferase activity, i.e., human FcεFI β-chain gene promoter activity increased in a pCR3.1-hMZF-1 antisense concentration-dependent manner. The fact that MZF-1 identified in Example 3 represses promoter activity by binding to the specified DNA sequence was verified by these results.

EXAMPLE 5

Increase in β-chain mRNA Due to Introduction of MZF-1 Antisense in KU812 Cells

Amounts of 20 μg of pCR3.1-hMZF-1 antisense or PCR3.1-self were introduced into KU812 cells by electroporation in the same manner as described in Example 1. After the cells were cultured for 12 h at 37° C. in a 5% CO$_2$ atmosphere, G418 was added to a final concentration of 0.4 mg/mL to select the cells into which the DNA had been introduced. The cells were cultured for an additional 48 h, and collected, and total RNA was prepared using TRIZOL (Invitrogen). Measurement of FcεFI β-chain and β-actin mRNA amounts were performed by RT-PCR using 1 μg of total RNA as a template for each. PCR was performed in cycles of 30 sec at 94° C., 30 sec at 55° C., and 1 min at 72° C. for 28-32 cycles for the β-chain and 18-22 cycles for the β-actin using 1 μL of the RT product as a template for each. The primers used in the PCR reaction are as follows:

β-chain:
5'-ATGGACACAGAAAGTAATAGGAGAG-3'    (SEQ ID NO: 6)

5'-CTTATAAATCAATGGGAGGAGACATT-3'   (SEQ ID NO: 7)

β-actin:
5'-CATCGAGCACGGCATCGTCACCAAC-3'    (SEQ ID NO: 8)

5'-GTGTTGGCGTACAGGTCTTTGCGGA-3'    (SEQ ID NO: 9)

Figure 5A:
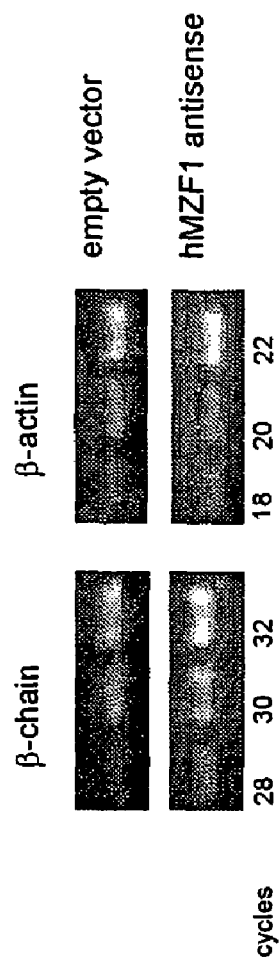
FIGS. 5 (A) and (B) show an increase in the amount of human FcεFI β-chain mRNA due to the introduction of an MZF-1 antisense in the present invention.

It was clear that the amount of β-chain mRNA was increased by introduction of the MZF-1 antisense. In addition, because the intensity of the β-actin band showed almost no change, it is believed that the transcription activation effect is specific to the β-chain (FIG. 5(A)).

Figure 5B:
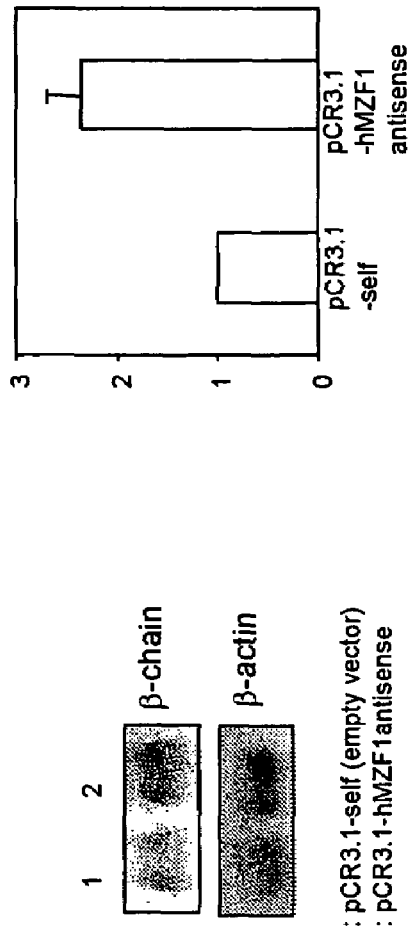

In addition, 10 μg of pCR3.1-hMZF-1 antisense or pCR3.1-self were introduced into KU812 cells in the same manner, and the cells into which the DNA had been introduced were selected by G418. Total RNA was prepared from the collected cells, and the amounts of FcεFI β-chain and β-actin mRNA were measured by Northern blotting. Electrophoresis was performed of 10 μg of total RNA using a 1.5% agarose gel containing 2.2 M formaldehyde, and the resultant was transferred to a Hybond-N(+) nylon membrane (Amersham Bioscience). Hybridization with probes for the FcεFI β-chain and β-actin labeled with DIG was performed in 5×SSC buffer containing 50% formamide, 1 % blocking reagent (Roche Diagnostics), 0.1 % N-lauroil sarcosine, and 0.02% SDS. The hybridized probes were detected using anti-DIG antibody and CDP-Star® substrate (both Roche Diagnostics). FIG. 5(B) shows the results. The graph on the right side of (B) shows a numerical value for the intensity of the β-chain band after correction with the intensity of the β-actin band. The amount of β-chain mRNA was increased approximately 2.5 times by introduction of the MZF-1 antisense.

The above results demonstrate that FcεFI β-chain expression is increased by the intracellular inhibition of the expression of MZF-1 through introduction of the MZF-1 antisense.

INDUSTRIAL APPLICABILITY

The present invention provides the nucleotide sequence involved in the repression of transcription of the human FcεFI β-chain gene, and establishes a screening method and kit comprising the same for compounds or salts thereof that inhibit β-chain expression. As a result, the present invention enables the development of a novel agent for the prevention and treatment of an allergic disease to proceed.

---

We claim:

1. An isolated polynucleotide consisting of the nucleotide sequence of SEQ ID NO: 1 or the complement thereof, wherein said polynucleotide regulates the transcription of the human high-affinity immunoglobulin E receptor β-chain gene.

2. The polynucleotide according to claim 1 wherein the polynucleotide is DNA.

3. A vector consisting of the polynucleotide of claim 1.

4. A screening kit for compounds or salts thereof that regulate the transcription of the human high-affinity immunoglobulin E receptor β-chain gene, said kit comprising the vector of claim 3.

* * * * *